(12) United States Patent
Miyoshi et al.

(10) Patent No.: US 8,420,323 B2
(45) Date of Patent: Apr. 16, 2013

(54) NUCLEIC ACID AMPLIFICATION METHOD

(75) Inventors: Hayato Miyoshi, Kanagawa (JP);
Yoshihide Iwaki, Kanagawa (JP);
Toshihiro Mori, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 247 days.

(21) Appl. No.: 12/270,706

(22) Filed: Nov. 13, 2008

(65) Prior Publication Data

US 2009/0162903 A1   Jun. 25, 2009

(30) Foreign Application Priority Data

Nov. 14, 2007 (JP) ................. 2007-295337

(51) Int. Cl.
*C12Q 1/68* (2006.01)
*C12P 19/34* (2006.01)

(52) U.S. Cl.
USPC ........................................ 435/6.12; 435/91.2

(58) Field of Classification Search .......... None
See application file for complete search history.

(56) References Cited

U.S. PATENT DOCUMENTS 6,033,881 A   3/2000   Himmler et al.

FOREIGN PATENT DOCUMENTS

| EP | 0 971 039 A2 | 1/2000 |
|---|---|---|
| EP | 1 715 037 A1 | 10/2006 |
| EP | 1 837 408 A1 | 9/2007 |
| EP | 2 025 761 A1 | 2/2009 |
| EP | 2 025 763 A1 | 2/2009 |
| JP | 5-130870 A | 5/1993 |
| JP | 2002-233379 A | 8/2002 |
| WO | WO 97/00330 A2 | 1/1997 |
| WO | 11-509406 A | 8/1998 |

OTHER PUBLICATIONS

Abe, C. et al, "Detection of *Mycobacterium tuberculosis* in Clinical Specimens by Polymerase Chain Reaction and Gen-Probe Amplified *Mycobacterium tuberculosis* Direct Test," Journal of Clinical Microbiology, Dec. 1993, vol. 31, No. 12, pp. 3270-3274.
Compton, J., "Nucleic acid sequence-based amplification," Nature, Mar. 7, 1991, vol. 350, pp. 91-92.
Fire, A. et al, "Rolling replication of short DNA circles," Proc. Natl. Acad. Sci. USA, May 1995, vol. 92, pp. 4641-4645.
Notomi, T. et al, "Principles and applications of novel gene amplification method (LAMP method) Loop-mediated isothermal amplification (LAMP) of DNA," Bio Industry, 2001, vol. 18, No. 2, pp. 15-23.
European Office Action for Application No. 08019924.3 dated Nov. 9, 2012.

*Primary Examiner* — Kenneth R. Horlick
*Assistant Examiner* — David Thomas
(74) *Attorney, Agent, or Firm* — Birch, Stewart, Kolasch & Birch, LLP

(57) ABSTRACT

An object to be achieved by the present invention is to provide a nucleic acid amplification method by which a nucleic acid can be amplified using oligonucleotide primers and DNA polymerase. The present invention provides a nucleic acid amplification method which comprises performing incubation of a reaction solution containing at least one type of deoxynucleotide triphosphate, at least one type of DNA polymerase, at least two types of oligonucleotide primer, and the nucleic acid fragment as a template so as to perform a polymerase reaction that initiates from the 3' end of the primer and thus amplifying the nucleic acid fragment, wherein a tag sequence is added at the 5' end of the first oligonucleotide primer, and the tag sequence is a nucleotide sequence on the template nucleic acid fragment which is present downstream of the sequence which is substantially complementary with the 3' end region of the first oligonucleotide primer (a region where the first oligonucleotide is annealed to the template nucleic acid).

14 Claims, 9 Drawing Sheets

Lane 1 : 50bp ladder (Invitrogen)
Lane 2 : Amplified product synthesized by primer (1) and primer (4)

Lane 1 : 50bp ladder (Invitrogen)
Lane 2 : Amplified product synthesized by primer (2) and primer (4)

Lane 1 : 50bp ladder (Invitrogen)
Lane 2 : Amplified product synthesized by primer (3) and primer (4)

Lane 1: 50bp ladder (Invitrogen)
Lane 2: Amplified product synthesized by primer (5) and primer (9)
Lane 3: Amplified product synthesized by primer (6) and primer (9)
Lane 4: Amplified product synthesized by primer (7) and primer (9)
Lane 5: Amplified product synthesized by primer (8) and primer (9)

Fig.13

```
                                        Forward Primer
                                   ────────────────────────▶
5'- ATGGGGCAAC CCGGGAACGG CAGCGCCTTC TTGCTGGCAC CCAATAGAAG CCATGCGCCG -3'
3'- TACCCCGTTG GGCCCTTGCC GTCGCGGAAG AACGACCGTG GGTTATCTTC GGTACGCGGC -5'
                                                  ◀────────────────────
                                                       Reverse Primer 5'- GACCACGACG TCACGCAGGA AAGGGACGAG GTGTGGGTGG TGGGCATGGG CATCGTCATG -3'
3'- CTGGTGCTGC AGTGCGTCCT TTCCCTGCTC CACACCCACC ACCCGTACCC GTAGCAGTAC -5'
```

Fig.14

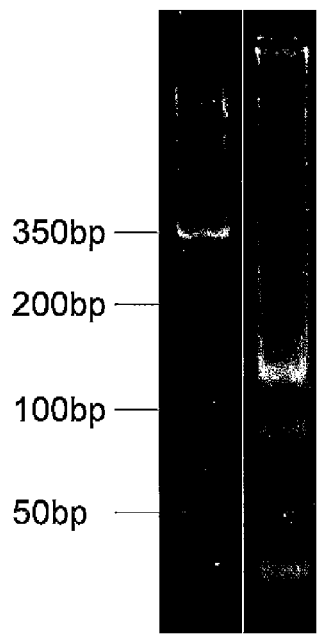

SEQUENCE LISTING

<160> NUMBER OF SEQ ID NOS: 31

<210> SEQ ID NO 1
<211> LENGTH: 25
<212> TYPE: DNA
<213> ORGANISM: Artificial Sequence
<220> FEATURE:
<223> OTHER INFORMATION: Synthetic DNA

<400> SEQUENCE: 1
ccacgacgct tgctggcacc caata                                            25

<210> SEQ ID NO 2
<211> LENGTH: 25
<212> TYPE: DNA
<213> ORGANISM: Artificial Sequence
<220> FEATURE:
<223> OTHER INFORMATION: Synthetic DNA

<400> SEQUENCE: 2
ggcaggaact tgctggcacc caata                                            25

<210> SEQ ID NO 3
<211> LENGTH: 25
<212> TYPE: DNA
<213> ORGANISM: Artificial Sequence
<220> FEATURE:
<223> OTHER INFORMATION: Synthetic DNA

<400> SEQUENCE: 3
tgggtggtct tgctggcacc caata                                            25

<210> SEQ ID NO 4
<211> LENGTH: 14
<212> TYPE: DNA
<213> ORGANISM: Artificial Sequence
<220> FEATURE:
<223> OTHER INFORMATION: Synthetic DNA

<400> SEQUENCE: 4
ccggcgcatg gctt                                                        14

<210> SEQ ID NO 5
<211> LENGTH: 17

```
<212> TYPE: DNA
<213> ORGANISM: Artificial Sequence
<220> FEATURE:
<223> OTHER INFORMATION: Synthetic DNA

<400> SEQUENCE: 5
caggaaacag ctatgac                                                            17

<210> SEQ ID NO 6
<211> LENGTH: 42
<212> TYPE: DNA
<213> ORGANISM: Artificial Sequence
<220> FEATURE:
<223> OTHER INFORMATION: Synthetic amplified product

<400> SEQUENCE: 6
ccacgacgtt cttgctggca cccaatagaa gccatgcgcc gg                                 42

<210> SEQ ID NO 7
<211> LENGTH: 85
<212> TYPE: DNA
<213> ORGANISM: Artificial Sequence
<220> FEATURE:
<223> OTHER INFORMATION: Synthetic amplified product

<400> SEQUENCE: 7
ccacgacgtt cttgctggca cccaatagaa gccatgcgcc ggaccacgac gttcttgctg             60
gcacccaata gaagccatgc gccgg                                                   85

<210> SEQ ID NO 8
<211> LENGTH: 128
<212> TYPE: DNA
<213> ORGANISM: Artificial Sequence
<220> FEATURE:
<223> OTHER INFORMATION: Synthetic amplified product

<400> SEQUENCE: 8
ccacgacgtt cttgctggca cccaatagaa gccatgcgcc ggaccacgac gttcttgctg             60
gcacccaata gaagccatgc gccggaccac gacgttcttg ctggcaccca atagaagcca           120
tgcgccgg                                                                    128

<210> SEQ ID NO 9
<211> LENGTH: 42
<212> TYPE: DNA
<213> ORGANISM: Artificial Sequence
<220> FEATURE:
<223> OTHER INFORMATION: Synthetic amplified product

<400> SEQUENCE: 9
gggacgagtt cttgctggca cccaatagaa gccatgcgcc gg                                 42

<210> SEQ ID NO 10
<211> LENGTH: 105
<212> TYPE: DNA
<213> ORGANISM: Artificial Sequence
<220> FEATURE:
<223> OTHER INFORMATION: Synthetic amplified product

<400> SEQUENCE: 10
gggacgagtt cttgctggca cccaatagaa gccatgcgcc ggaccacgac gtcacgcagg             60
aaagggacga gttcttgctg gcacccaata gaagccatgc gccgg                            105

<210> SEQ ID NO 11
<211> LENGTH: 168
```

```
<212> TYPE: DNA
<213> ORGANISM: Artificial Sequence
<220> FEATURE:
<223> OTHER INFORMATION: Synthetic amplified product

<400> SEQUENCE: 11
gggacgagtt cttgctggca cccaatagaa gccatgcgcc ggaccacgac gtcacgcagg    60
aaagggacga gttcttgctg gcacccaata gaagccatgc gccggaccac gacgtcacgc   120
aggaaaggga cgagttcttg ctggcaccca atagaagcca tgcgccgg               168

<210> SEQ ID NO 12
<211> LENGTH: 42
<212> TYPE: DNA
<213> ORGANISM: Artificial Sequence
<220> FEATURE:
<223> OTHER INFORMATION: Synthetic amplified product

<400> SEQUENCE: 12
tgggtggttt cttgctggca cccaatagaa gccatgcgcc gg                      42

<210> SEQ ID NO 13
<211> LENGTH: 116
<212> TYPE: DNA
<213> ORGANISM: Artificial Sequence
<220> FEATURE:
<223> OTHER INFORMATION: Synthetic amplified product

<400> SEQUENCE: 13
tgggtggttt cttgctggca cccaatagaa gccatgcgcc ggaccacgac gtcacgcagg    60
aaagggacga ggtgtgggtg gtttcttgct ggcacccaat agaagccatg cgccgg       116

<210> SEQ ID NO 14
<211> LENGTH: 190
<212> TYPE: DNA
<213> ORGANISM: Artificial Sequence
<220> FEATURE:
<223> OTHER INFORMATION: Synthetic amplified product

<400> SEQUENCE: 14
tgggtggttt cttgctggca cccaatagaa gccatgcgcc ggaccacgac gtcacgcagg    60
aaagggacga ggtgtgggtg gtttcttgct ggcacccaat agaagccatg cgccggacca   120
cgacgtcacg caggaaaggg acgaggtgtg gtggtttct tgctggcacc caatagaagc    180
catgcgccgg                                                          190

<210> SEQ ID NO 15
<211> LENGTH: 21
<212> TYPE: DNA
<213> ORGANISM: Artificial Sequence
<220> FEATURE:
<223> OTHER INFORMATION: Synthetic DNA

<400> SEQUENCE: 15
tggtcttgct ggcacccaat a                                             21

<210> SEQ ID NO 16
<211> LENGTH: 25
<212> TYPE: DNA
<213> ORGANISM: Artificial Sequence
<220> FEATURE:
<223> OTHER INFORMATION: Synthetic DNA

<400> SEQUENCE: 16
tgggtggtct tgctggcacc caata                                         25
```

<210> SEQ ID NO 17
<211> LENGTH: 29
<212> TYPE: DNA
<213> ORGANISM: Artificial Sequence
<220> FEATURE:
<223> OTHER INFORMATION: Synthetic DNA

<400> SEQUENCE: 17
tgggtggtgg gccttgctgg cacccaata                                29

<210> SEQ ID NO 18
<211> LENGTH: 31
<212> TYPE: DNA
<213> ORGANISM: Artificial Sequence
<220> FEATURE:
<223> OTHER INFORMATION: Synthetic DNA

<400> SEQUENCE: 18
tgggtggtgg gcatcttgct ggcacccaat a                             31

<210> SEQ ID NO 19
<211> LENGTH: 17
<212> TYPE: DNA
<213> ORGANISM: Artificial Sequence
<220> FEATURE:
<223> OTHER INFORMATION: Synthetic DNA

<400> SEQUENCE: 19
tccctttcct gcgtgac                                             17

<210> SEQ ID NO 20
<211> LENGTH: 17
<212> TYPE: DNA
<213> ORGANISM: Artificial Sequence
<220> FEATURE:
<223> OTHER INFORMATION: Synthetic DNA

<400> SEQUENCE: 20
cttgctggca cccaata                                             17

<210> SEQ ID NO 21
<211> LENGTH: 42
<212> TYPE: DNA
<213> ORGANISM: Artificial Sequence
<220> FEATURE:
<223> OTHER INFORMATION: Synthetic DNA

<400> SEQUENCE: 21
ccggcgcatg gcttctattg ggtgccagca agaacgtcgt gg                 42

<210> SEQ ID NO 22
<211> LENGTH: 85
<212> TYPE: DNA
<213> ORGANISM: Artificial Sequence
<220> FEATURE:
<223> OTHER INFORMATION: Synthetic DNA

<400> SEQUENCE: 22
ccggcgcatg gcttctattg ggtgccagca agaacgtcgt ggtccggcgc atggcttcta    60 tgggtgcca gcaagaacgt cgtgg                                          85

<210> SEQ ID NO 23
<211> LENGTH: 128
<212> TYPE: DNA
<213> ORGANISM: Artificial Sequence

```
<220> FEATURE:
<223> OTHER INFORMATION: Synthetic DNA

<400> SEQUENCE: 23
ccggcgcatg gcttctattg ggtgccagca agaacgtcgt ggtccggcgc atggcttcta      60
ttgggtgcca gcaagaacgt cgtggtccgg cgcatggctt ctattgggtg ccagcaagaa     120
cgtcgtgg                                                              128

<210> SEQ ID NO 24
<211> LENGTH: 42
<212> TYPE: DNA
<213> ORGANISM: Artificial Sequence
<220> FEATURE:
<223> OTHER INFORMATION: Synthetic DNA

<400> SEQUENCE: 24
ccggcgcatg gcttctattg ggtgccagca agaagagcag gg                         42

<210> SEQ ID NO 25
<211> LENGTH: 105
<212> TYPE: DNA
<213> ORGANISM: Artificial Sequence
<220> FEATURE:
<223> OTHER INFORMATION: Synthetic DNA

<400> SEQUENCE: 25
ccggcgcatg gcttctattg ggtgccagca agaactcgtc cctttcctgc gtgacgtcgt      60
ggtccggcgc atggcttcta ttgggtgcca gcaagaactc gtccc                     105

<210> SEQ ID NO 26
<211> LENGTH: 168
<212> TYPE: DNA
<213> ORGANISM: Artificial Sequence
<220> FEATURE:
<223> OTHER INFORMATION: Synthetic DNA

<400> SEQUENCE: 26
ccggcgcatg gcttctattg ggtgccagca agaactcgtc cctttcctgc gtgacgtcgt      60
ggtccggcgc atggcttcta ttgggtgcca gcaagaactc gtccctttcc tgcgtgacgt     120
cgtggtccgg cgcatggctt ctattgggtg ccagcaagaa ctcgtccc                  168

<210> SEQ ID NO 27
<211> LENGTH: 42
<212> TYPE: DNA
<213> ORGANISM: Artificial Sequence
<220> FEATURE:
<223> OTHER INFORMATION: Synthetic DNA

<400> SEQUENCE: 27
ccggcgcatg gcttctattg ggtgccagca agaaaccacc ca                         42

<210> SEQ ID NO 28
<211> LENGTH: 116
<212> TYPE: DNA
<213> ORGANISM: Artificial Sequence
<220> FEATURE:
<223> OTHER INFORMATION: Synthetic DNA

<400> SEQUENCE: 28
ccggcgcatg gcttctattg ggtgccagca agaaaccacc cacacctcgt ccctttcctg      60
cgtgacgtcg tggtccggcg catggcttct attgggtgcc agcaagaaac caccca         116
```

```
<210> SEQ ID NO 29
<211> LENGTH: 190
<212> TYPE: DNA
<213> ORGANISM: Artificial Sequence
<220> FEATURE:
<223> OTHER INFORMATION: Synthetic DNA

<400> SEQUENCE: 29
ccggcgcatg gcttctattg ggtgccagca agaaaccacc cacacctcgt cccttcctg      60 cgtgacgtcg tggtccggcg catggcttct attgggtgcc agcaagaaac cacccacacc    120
tcgtcccttt cctgcgtgac gtcgtggtcc ggcgcatggc ttctattggg tgccagcaag    180
aaaccaccca                                                           190

<210> SEQ ID NO 30
<211> LENGTH: 120
<212> TYPE: DNA
<213> ORGANISM: Artificial Sequence
<220> FEATURE:
<223> OTHER INFORMATION: Synthetic DNA

<400> SEQUENCE: 30
atggggcaac ccgggaacgg cagcgccttc ttgctggcac ccaatagaag ccatgcgccg     60
gaccacgacg tcacgcagga aagggacgag gtgtgggtgg tgggcatggg catcgtcatg    120

<210> SEQ ID NO 31
<211> LENGTH: 120
<212> TYPE: DNA
<213> ORGANISM: Artificial Sequence
<220> FEATURE:
<223> OTHER INFORMATION: Synthetic DNA

<400> SEQUENCE: 31
catgacgatg cccatgccca ccacccacac ctcgtccctt tcctgcgtga cgtcgtggtc     60
cggcgcatgg cttctattgg gtgccagcaa gaaggcgctg ccgttcccgg gttgccccat    120
```

NUCLEIC ACID AMPLIFICATION METHOD

TECHNICAL FIELD

The present invention relates to a nucleic acid amplification method. More specifically, the present invention relates to a nucleic acid amplification method that comprises performing a polymerase reaction through incubation of a reaction solution using DNA polymerase.

BACKGROUND ART

In molecular biological research, nucleic acid amplification is generally performed by an enzymatic method using DNA polymerase. Polymerase chain reaction (PCR) is broadly known as a nucleic acid amplification method. For amplification of a target nucleic acid sequence, the PCR method comprises the three steps of: denaturing (denaturation step) double-stranded DNA as a template into single-stranded DNAs; annealing (annealing step) primers to the single-stranded DNAs; and elongating (elongation step) complementary strands using the primers as origins. According to a general PCR method, the denaturation step, the annealing step, and the elongation step are each performed at different temperatures using a thermal cycler. However, implementation of nucleic acid amplification reactions at three different types of temperature is problematic in that temperature control is complicated and time loss increases in proportion to the number of cycles.

Hence, nucleic acid amplification methods that can be performed under isothermal conditions have been developed. Examples of such methods include RCA (Rolling Circle Amplification: Proc. Natl. Acad. Sci, vol. 92, 4641-4645 (1995)), ICAN (Isothermal and Chimeric primer-initiated Amplification of Nucleic acids), LAMP (Loop-Mediated Isothermal Amplification of DNA; Bio Industry, vol. 18, No. 2 (2001)), NASBA (Nucleic acid Sequence-based Amplification method; Nature, 350, 91-(1991)), and TMA (Transcription mediated amplification method; J. Clin Microbiol. Vol. 31, 3270-(1993)).

An SDA method (JP Patent Publication (Kokai) No. 5-130870 A (1993)) is a cycling assay method using exonuclease, which is a method for amplifying a target site of a target nucleic acid fragment using a polymerase elongation reaction. This method comprises performing a polymerase elongation reaction using primers (as origins) that have specifically hybridized to target sites of target nucleic acid fragments, while causing 5'→3' exonuclease to act thereon, so as to degrade the primers from the opposite directions. New primers undergo hybridization instead of the degraded primers, so that another elongation reaction proceeds again with the use of DNA polymerase. Such an elongation reaction with the use of polymerase and such a degradation reaction with the use of exonuclease by which the strand that has been elongated is removed are repeated periodically in order. Here, the elongation reaction with the use of polymerase and the degradation reaction with the use of exonuclease can be implemented under isothermal conditions. However, the use of exonuclease in addition to polymerase is required, and thus the method is expensive and the design of primers should be improved.

A LAMP method is a method for amplifying target sites of a target nucleic acid fragment that has been developed in recent years. This method is a method for amplifying target sites of a target nucleic acid fragment as special structure which is complementary to the elongated region from the 3' terminal by 5' terminal of the primer, under isothermal conditions through the use of at least four types of primer that complementarily recognize at least six specific sites of a target nucleic acid fragment and strand-displacement-type Bst DNA polymerase lacking 5'→3' nuclease activity and catalyzing an elongation reaction while liberating double-stranded DNA on the template in the form of single-stranded DNAs. However, the method requires the use of at least four types of primer that recognize six specific sites, so that the design of primers is very difficult.

An ICAN method is a method for amplifying target sites of a target nucleic acid fragment that has been developed in recent years. The ICAN method is an isothermal gene amplification method using RNA-DNA chimeric primers, DNA polymerase having strand displacement activity and template exchange activity, and RNaseH. After chimeric primers bind to a template, a complementary strand is synthesized by DNA polymerase. Subsequently, RNaseH cleaves RNA portions derived from the chimeric primers and then an elongation reaction accompanied by a strand displacement reaction and a template exchange reaction takes place repeatedly from the cleaved sites, so that the gene amplification is performed. However, this method also requires the use of special primers that are chimeric primers and thus the design of such primers is very difficult.

JP Patent Publication (Kohyo) No. 11-509406 A discloses an amplification method, by which, in the presence of DNA polymerase capable of strand displacement, DNA within a target region is amplified by an isothermal reaction using at least a set of oligonucleotide primers. However, the method disclosed in JP Patent Publication (Kohyo) No. 11-509406 A is problematic in that it requires a relatively long reaction time, for example.

JP Patent Publication (Kokai) No. 2002-233379 A discloses an amplification method, by which, in the presence of DNA polymerase capable of strand displacement, DNA within a target region is amplified by an isothermal reaction using at least a set of oligonucleotide primers. However, the method disclosed in JP Patent Publication (Kokai) No. 2002-233379 A is problematic in that non-specifically amplified product is generated outstandingly.

DISCLOSURE OF THE INVENTION

An object to be achieved by the present invention is to provide a nucleic acid amplification method by which a nucleic acid can be amplified using oligonucleotide primers and DNA polymerase. Furthermore, an object to be achieved by the present invention is to provide a simple and rapid method for nucleic acid amplification by which a target nucleic acid sequence can be specifically amplified in a short time and a high efficiency.

As a result of intensive studies to achieve the above objects, the present inventors have succeeded in specifically amplifying a target nucleic acid only by adding, at the 5' end of the first oligonucleotide primer, a nucleotide sequence on the template nucleic acid fragment which is present downstream of the sequence which is substantially identical with the first oligonucleotide primer, in a nucleic acid amplification method which comprises performing incubation of a reaction solution containing at least one type of deoxynucleotide triphosphate, at least one type of DNA polymerase, at least two types of oligonucleotide primer, and the nucleic acid fragment as a template so as to perform a polymerase reaction that initiates from the 3' end of the primer and thus amplifying the nucleic acid fragment.

Specifically, the present invention provides a nucleic acid amplification method which comprises performing incubation of a reaction solution containing at least one type of deoxynucleotide triphosphate, at least one type of DNA polymerase, at least two types of oligonucleotide primer, and the nucleic acid fragment as a template so as to perform a polymerase reaction that initiates from the 3' end of the primer and thus amplifying the nucleic acid fragment, wherein a tag sequence is added at the 5' end of the first oligonucleotide primer, and the tag sequence is a nucleotide sequence on the template nucleic acid fragment which is present downstream of the sequence which is substantially identical with the 3' end region (a region where the first oligonucleotide is annealed to the template nucleic acid) of the first oligonucleotide primer. FIG. 1 shows the positional relationship of the first oligonucleotide primer, the second oligonucleotide primer and the tag sequence.

Preferably, the 3' end nucleotide of the tag sequence is a nucleotide on the template nucleic acid fragment which is present downstream of the sequence which is substantially complementary to the second oligonucleotide primer FIG. 2 shows the positional relationship of the first oligonucleotide primer, the second oligonucleotide primer and the tag sequence.

Preferably, the tag sequence is a nucleotide sequence on the template nucleic acid fragment which is present downstream of the sequence which is substantially complementary to the second oligonucleotide primer. FIG. 3 shows the positional relationship of the first oligonucleotide primer, the second oligonucleotide primer and the tag sequence.

Preferably, the tag sequence which is added to the 5' end side of the first oligonucleotide primer is 2 to 20 nucleotides.

Preferably, the tag sequence which is added to the 5' end of the first oligonucleotide primer is a nucleotide sequence on the template nucleic acid fragment which is present within the region of 200 or less nucleotides downstream of the sequence which is substantially identical with the 3' end region (a region where the first oligonucleotide is annealed to the template nucleic acid) of the first oligonucleotide primer.

Preferably, the reaction solution further contains at least 0.01% or more surfactant.

Preferably, the surfactant is a nonionic surfactant.

Preferably, the nonionic surfactant is selected from among a polyoxyethylene sorbitan fatty acid ester-based surfactant, a polyoxyethylene alkylphenol ether-based surfactant, and a polyoxyethylene alkyl ether-based surfactant.

Preferably, the reaction solution Her contains a divalent cation.

Preferably, the reaction solution further contains a melting temperature adjusting agent.

Preferably, the melting temperature adjusting agent is dimethyl sulfoxide, betaine, formamide, or glycerol, or a mixture of two or more types thereof.

Preferably, the at least one type of DNA polymerase is a DNA polymerase having strand displacement activity.

Preferably, at least one type of the polymerase having strand displacement activity is polymerase selected from the group consisting of *Bacillus stearothermophilus*-derived 5'→3' exonuclease-deficient Bst. DNA polymerase, *Bacillus caldotenax*-derived 5'→3' exonuclease-deficient Bca DNA polymerase, *Thermococcus litoralis*-derived 5'→3' exonuclease-deficient Vent. DNA polymerase, and *Alicyclobacillus acidocaldarius*-derived DNA polymerase.

Preferably, the step of amplification of nucleic acid is performed substantially isothermally.

Preferably, the step of amplification of nucleic acid is performed at a temperature of 50° C. to 100° C.

Preferably, the step of amplification of nucleic acid is performed substantially within 60 minutes.

According to the present invention, a polymer (high molecular) product is very efficiently generated via the tag sequence which is added to the 5' end of the first oligonucleotide primer (namely, a nucleotide sequence on the template nucleic acid fragment which is present downstream of the sequence which is substantially identical with the 3' end region (a region where the first oligonucleotide is annealed to the template nucleic acid) of the first oligonucleotide primer), and therefore only a target nucleic acid sequence can be specifically amplified. Further, according to the present invention, a target nucleic acid can be amplified without a complicated temperature control, use of special enzyme, and complicated design of primers, and therefore a simple, rapid and high sensitive method for amplification of nucleic acid is provided.

BRIEF DESCRIPTION OF THE DRAWINGS

FIG. 13 shows in detail the positional relationship of the primers used in the Examples and β2AR gene (SEQ ID NOS: 30 and 31).

FIG. 14 shows the results of electrophoresis of an amplified product obtained as a result of the amplification reaction of the present invention.

FIG. 11 shows in detail the positional relationship of the primers used in the Examples and β2AR gene.

PREFERRED EMBODIMENT OF THE INVENTION

The present invention will be further described in detail as follows.

The nucleic acid amplification method of the present invention comprises performing incubation of a reaction solution containing at least one type of deoxynucleotide triphosphate, at least one type of DNA polymerase, at least two types of oligonucleotide primer, and the nucleic acid fragment as a template so as to perform a polymerase reaction that initiates from the 3' end of the primer and thus amplifying the nucleic acid fragment, and is characterized in that a tag sequence is added at the 5' end of the first oligonucleotide primer, and the tag sequence is a nucleotide sequence on the template nucleic acid fragment which is present downstream of the sequence which is substantially identical with the 3' end region of the first oligonucleotide primer (the region of the first oligonucleotide primer where it is annealed to the template nucleic acid).

Figure 1:
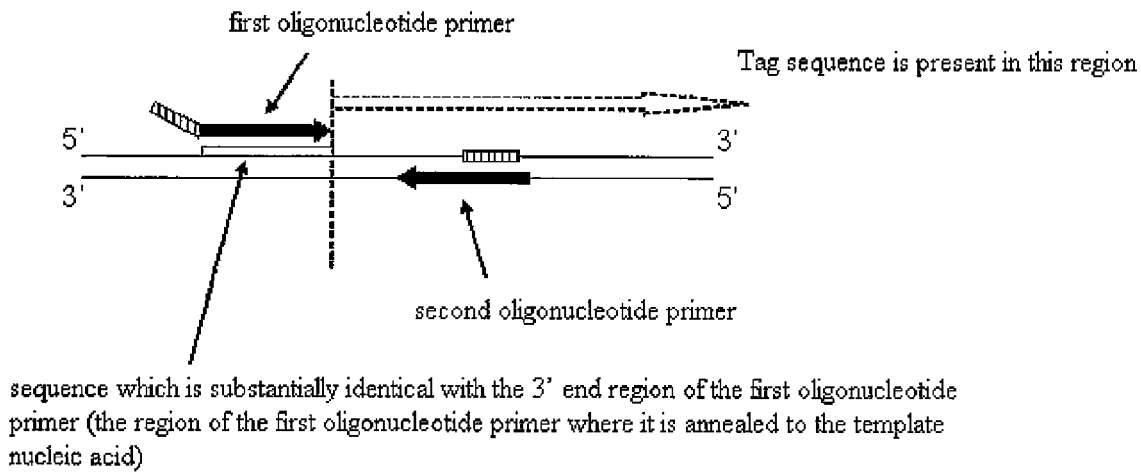
FIG. 1 shows the positional relationship of the primers and the tag sequence in the present invention.
Figure 2:
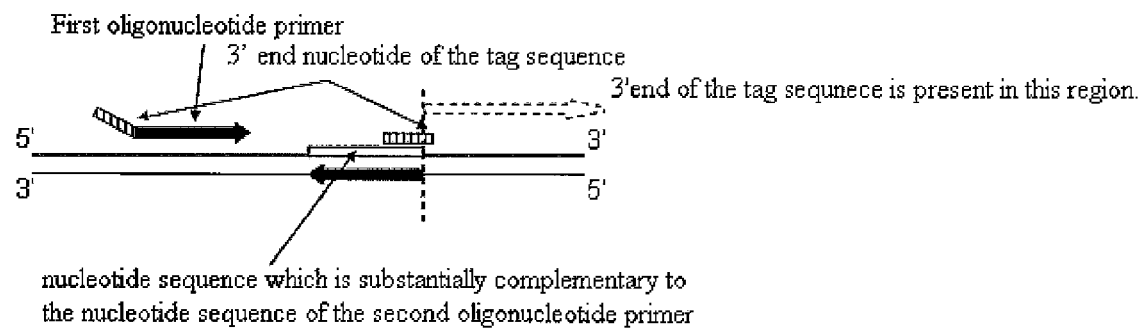
FIG. 2 shows the positional relationship of the primers and the tag sequence in the present invention.
Figure 3:
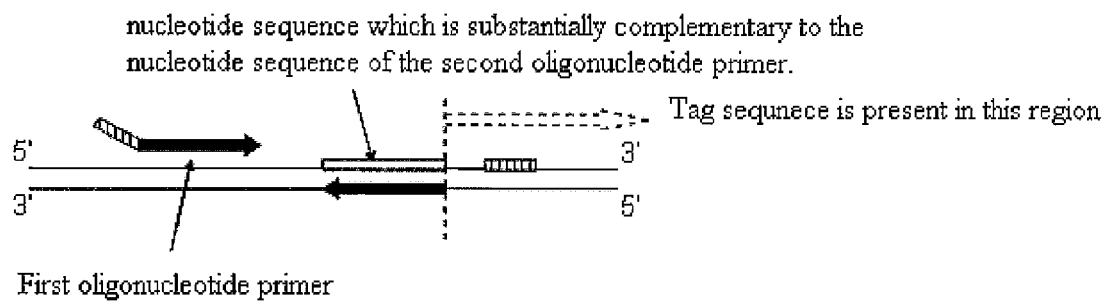
FIG. 3 shows the positional relationship of the primers and the tag sequence in the present invention.
Figure 4:
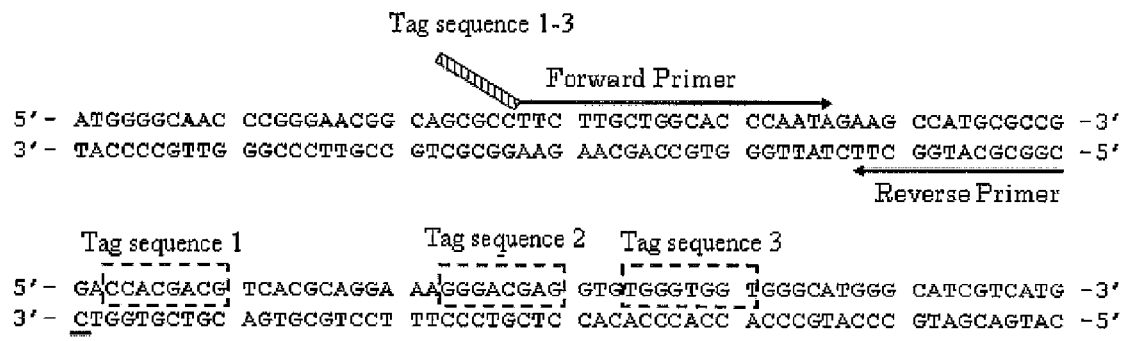
FIG. 4 shows in detail the positional relationship of the primers used in the Examples and β2AR gene (SEQ ID NOS: 30 and 31).

FIG. 4 shows in detail the positional relationship of the primers used in the Example 1 which is one embodiment of the present invention and β2AR gene. In Example 1, the tag sequence which is added at the 5' end of the first oligonucleotide primer (SEQ ID NO.1) is 5'-CCACGACG-3' (SEQ ID NO:1 and FIG. 4). The sequence which is substantially complementary with the 3' terminal side region (a region where the first oligonucleotide is annealed to the template nucleic acid) of the first oligonucleotide primer on the nucleotide sequence of the template nucleic acid fragment corresponds to 5'-CTTGCTGGCACCCAATA-3' (SEQ ID NO: 20). The nucleotide sequence on the template nucleic acid fragment which is present downstream of the sequence which is substantially identical with the 3' end region of the first oligonucleotide primer (the region of the first oligonucleotide primer where it is annealed to the template nucleic acid) corresponds to 5'-CCACGACG-3'(FIG. 4), and this nucleotide sequence corresponds to the tag sequence which is added at the 5' end of the first oligonucleotide primer (SEQ ID NO.1).

Figure 15:
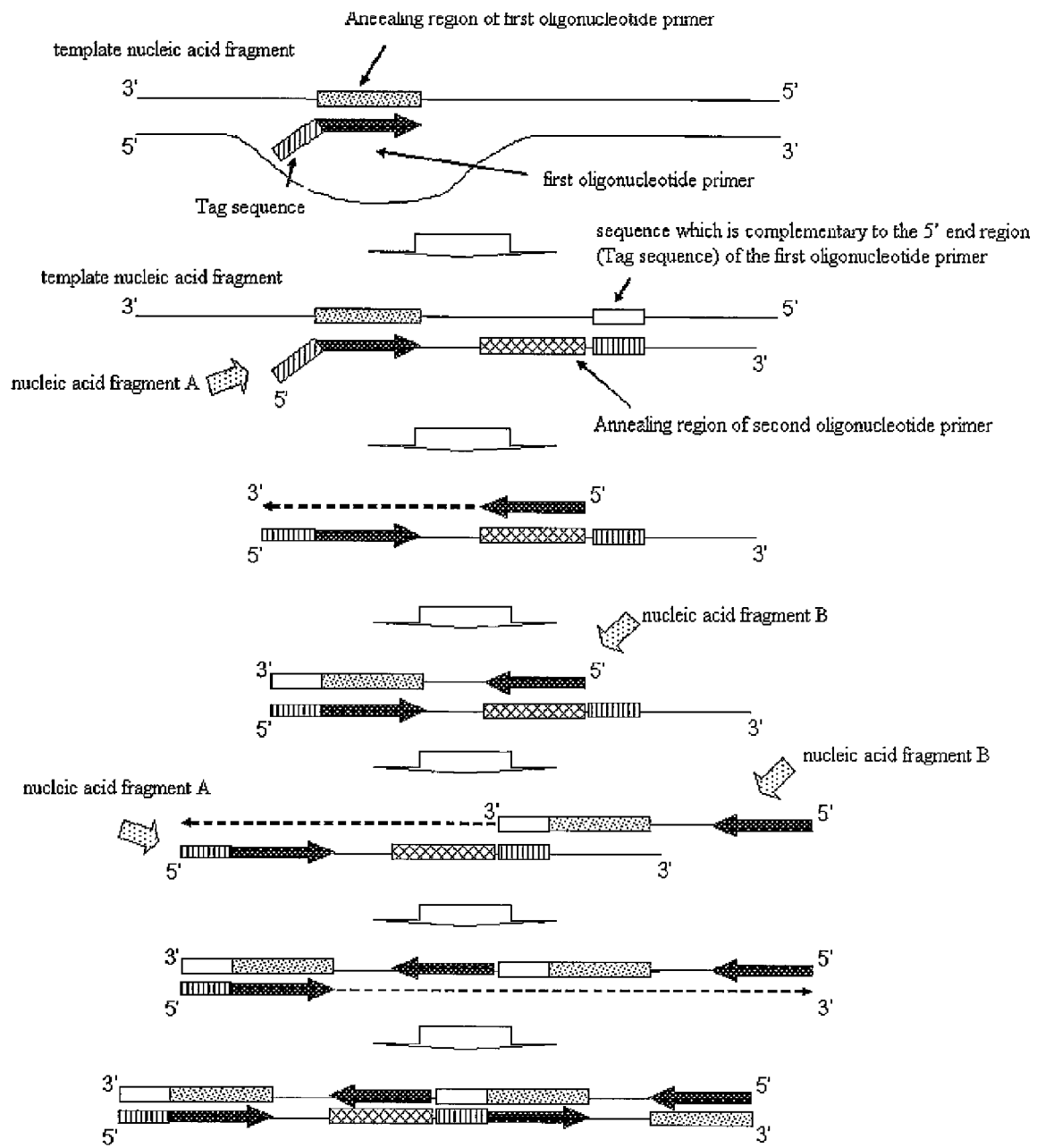
FIG. 15 shows the mechanism for the formation of an amplified product in the present invention.

The outline of the nucleic acid amplification method of the present invention is shown in FIG. 15. The first oligonucleotide primer is annealed to a template nucleic acid strand, and the polymerase reaction is initiated from the 3' end of the oligonucleotide primer. Because a tag sequence (nucleotide sequence on the template nucleic acid fragment which is present downstream of the sequence which is substantially identical with the 3' end region of the first oligonucleotide primer (the region of the first oligonucleotide primer where it is annealed to the template nucleic acid)) is added at the 5' end of the first oligonucleotide primer, an amplified nucleic acid fragment which contains the tag sequence at its 5' end is obtained as an amplified product of the polymerase reaction which initiates from the first oligonucleotide primer. (This amplified product is referred to as a nucleic acid fragment A)

Then, the second oligonucleotide primer is annealed to the nucleic acid fragment A which was obtained above, and the polymerase reaction is initiated from the 3' end of the oligonucleotide primer. At this moment, the tag sequence (nucleotide sequence on the template nucleic acid fragment which is present downstream of the sequence which is substantially identical with the 3' end region of the first oligonucleotide primer (the region of the first oligonucleotide primer where it is annealed to the template nucleic acid)) is present at the 5' terminal of the amplified nucleic acid fragment A which is a template. Therefore, the sequence which is substantially complementary to the tag sequence (nucleotide sequence on the template nucleic acid fragment which is present downstream of the sequence which is substantially identical with the 37 end region of the first oligonucleotide primer (the region of the first oligonucleotide primer where it is annealed to the template nucleic acid)) is contained at the 3' end of the obtained amplified nucleic acid fragment (this is referred to as a nucleic acid fragment B).

The 3' end sequence of the nucleic acid fragment B is complementary with the sequence contained in the nucleic acid fragment A at two sites. The 3' end of the nucleic acid fragment B forms a double strand with a complementary sequence which is present at the 3' end side of the nucleic acid fragment A, and polymerase reaction which initiates Thom this starts, and thus polymer (high molecular) amplified nucleic acid fragments are synthesized.

In the same way, the obtained polymer Nigh molecular) amplified nucleic acid fragment forms a double strand with a complementary sequence which is present at the 3' end side of the nucleic acid fragment A, and polymerase reaction which initiates from this starts, and thus further polymer (high molecular) amplified nucleic acid fragments can be synthesized.

Hereinafter, ingredients that are used in the present invention will be explained.

(1) Deoxynucleotide Triphosphate

Deoxynucleotide triphosphate is used as a substrate for an elongation reaction. Specifically, a mixture of dATP, dCTP, dCTP, and dTTP is preferably used. Deoxynucleotide triphosphate to be used herein may contain a dNTP analog (e.g., 7-deaza-dGTP).

Furthermore, deoxynucleotide triphosphate (dATP, dCTP, dGTP, or dTTP mixture) is at a final concentration ranging from 0.1 mM to 3.0 mM, preferably 0.75 mM to 3.0 mM, further preferably 1.0 mM to 2.0 mM, and particularly preferably 1.0 mM to 1.5 mM.

(2) DNA Polymerase

In the present invention, DNA polymerase is used. Preferably, polymerase capable of strand displacement (or having strand displacement activity) can be used as the DNA polymerase. In the description, "strand displacement activity" refers to activity by which strand displacement can be performed; that is, when DNA replication is performed based on a template nucleic acid sequence, strand displacement proceeds by replacement of DNA strands, so as to liberate a complementary strand that has annealed to the template strand. Specific examples of polymerase capable of strand displacement include, but are not limited to, *Bacillus stearothermophilus*-derived 5'→3' exonuclease-deficient list. DNA polymerase, *Bacillus caldotenax*-derived 5'→3' exonuclease-deficient Boa DNA polymerase, *Thermococcus litoralis*-derived 5'→3' exonuclease-deficient Vent. DNA polymerase, and *Alicyclobacillus acidocaldarius*-derived DNA polymerase. Such polymerase capable of strand displacement may be derived from nature or may be a genetically engineered recombinant protein.

(3) Divalent Cation

In the present invention, divalent cations may be used in response to metal requirements and the like regarding enzymes to be used herein. As divalent cations, magnesium salts or other metal salts can be used. For example, magnesium chloride, magnesium acetate, and magnesium sulfate can be used. Such a divalent cation is at a final concentration preferably ranging from 1 mM to 20 mM and further preferably ranging from 2 mM to 10 mM.

(4) Surfactant

In the present invention, a surfactant may be added to a reaction solution. An advantageous effect; that is, prevention of nonspecific nucleic acid amplification, is achieved via the use of a surfactant. Types of such surfactant that can be used in the present invention are not particularly limited, and may include the following:

anionic surfactants such as alkylbenzene sulfonate, lauryl sulfate (SDS), octyl sulfosuccinate, and stearic acid soap;

nonionic surfactants such as sucrose fatty acid ester, sorbitan fatty acid ester, POE sorbitan fatty acid ester (e.g., Tween 20, Tween 40, Tween 60, Tween 80, and the like), fatty acid alkanol amide, POE alkyl ether (e.g., Brij35, Brij58, and the like), POE alkyl phenyl ether (e.g., Triton X-100, Triton X-114, Nonidet P40, and the like), nonylphenol, lauryl alcohol, polyethylene glycol, polyoxyethylene·polyoxypropylene block polymer, POE alkyl amine, and POE fatty acid bisphenyl ether;

cationic surfactants such as cetylpyridium chloride, lauryl dimethylbenzyl ammonium chloride, and stearyltrimethylammonium chloride.

The dose of such a surfactant is not particularly limited, as long as the effects of the present invention can be achieved and is preferably 0.01% or more, more preferably 0.05% or more, and more preferably 0.1% or more. The upper limit of the dose of such a surfactant is not particularly limited and is generally 10% or less, preferably 5% or less, and more preferably 1% or less.

Among the above surfactants, nonionic surfactants are preferably used. Among the nonionic surfactants, highly hydrophilic surfactants are preferred. The HLB value is preferably 12 or more, and further preferably 14 or more. Preferably, the upper limit of HLB is 20. Preferably, the value of HLB is 17 or less. More preferably, the value of HLB is 14 to 17. The surfactant is preferably selected from a polyoxyethylene sorbitan fatty acid ester-based surfactant, and a polyoxyethylene alkyl ether-based surfactant. Among the polyoxyethylene sorbitan fatty acid ester, polyoxyethylene sorbitan mono fatty acid ester is preferred. Preferably the compound represented by the following formula can be used:

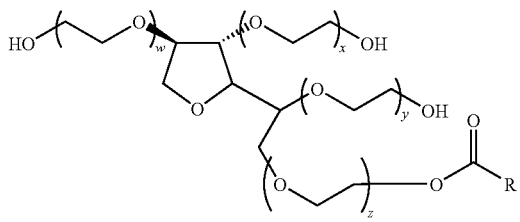

wherein $x+y+z+w=20$, R is an alkyl group having a carbon number of 12 to 18.

The position of the alkyl group is not particularly limited, and the compound of the following structure can be preferably used.

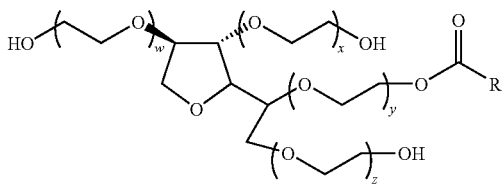

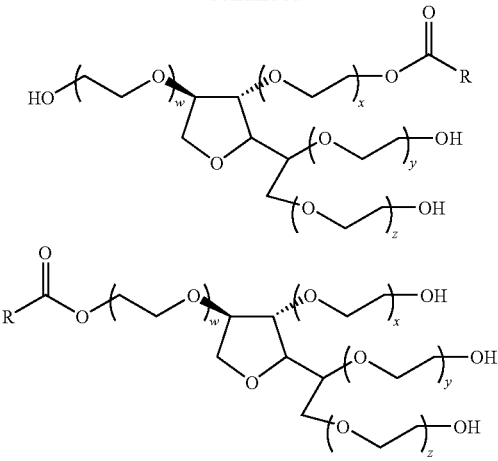

wherein $x+y+z+w=20$, R is an alkyl group having a carbon number of 12 to 18.

Specific examples of such surfactants may include polyoxyethylene(20) sorbitan monolaurate, polyoxyethylene(20) sorbitan monopalmitate, polyoxyethylene(20) sorbitan monostearate, and polyoxyethylene(20) sorbitan monooleate (trade name: Tween 20, Tween 40, Tween 60, Tween 80, and the like). The dose of such surfactant is not particularly limited, and may be preferably 0.01% or more, more preferably 0.05% or more, and more preferably 0.1% or more.

(5) Oligonucleotide Primer

The oligonucleotide primer to be used in the present invention has a nucleotide sequence substantially complementary to template DNA and has the 3' end from which DNA strand elongation is possible. Such oligonucleotide primer has a nucleotide sequence substantially complementary to template DNA, so that it can anneal to the template DNA. As an oligonucleotide primer to be used in the present invention, an oligonucleotide primer composed of a deoxyribonucleotide or a ribonucleotide can be used. Furthermore, an oligonucleotide primer containing a modified ribonucleotide or a modified deoxyribonucleotide may also be used herein.

In the present invention, a tag sequence (namely, a nucleotide sequence which is present at downstream of the sequence on the template nucleic acid fragment which is substantially identical with the 3' end region (a region where the first oligonucleotide is annealed to the template nucleic acid) of the first oligonucleotide primer) is added at the 5' end of the first oligonucleotide primer.

Preferably, the tag sequence which is added to the 5' end of the first oligonucleotide primer is 2 to 20 nucleotides.

Preferably, the tag sequence which is added to the 5' end of the first oligonucleotide primer is 2 to 16 nucleotides.

Preferably, the tag sequence which is added to the 5' end of the first oligonucleotide primer is 4 to 14 nucleotides.

Preferably, the tag sequence which is added to the 5' end of the first oligonucleotide primer is a nucleotide sequence on the template nucleic acid fragment which is present within the region of 200 or less nucleotides downstream of the sequence which is substantially identical with the 3' end region of the first oligonucleotide primer (the region of the first oligonucleotide primer where it is annealed to the template nucleic acid).

Preferably, the tag sequence which is added to the 5' end of the first oligonucleotide primer is a nucleotide sequence on the template nucleic acid fragment which is present within the region of 100 or less nucleotides downstream of the sequence which is substantially identical with the 3' end region of the first oligonucleotide primer (the region of the first oligonucleotide primer where it is annealed to the template nucleic acid).

Preferably, the tag sequence which is added to the 5' end of the first oligonucleotide primer is a nucleotide sequence on the template nucleic acid fragment which is present within the region of 60 or less nucleotides downstream of the sequence which is substantially identical with the 3' end region of the first oligonucleotide primer (the region of the first oligonucleotide primer where it is annealed to the template nucleic acid).

Preferably, the tag sequence which is added to the 5' end of the first oligonucleotide primer is a nucleotide sequence on the template nucleic acid fragment which is present within the region of 50 or less nucleotides downstream of the sequence which is substantially identical with the 3' end region of the first oligonucleotide primer (the region of the first oligonucleotide primer where ft is annealed to the template nucleic acid).

The length of an oligonucleotide primer is not particularly limited and generally ranges from approximately 10 to 100 nucleotides, preferably ranges from approximately 15 to 50 nucleotides, and further preferably ranges from approximately 15 to 40 nucleotides.

Oligonucleotide primers can be synthesized by the phosphoramidite method using a commercially available DNA synthesizer (e.g., Applied Biosystem Inc., DNA synthesizer 394).

The dose of an oligonucleotide primer is preferably 0.1 µM or more, further preferably 1 µM or more, and particularly preferably 1.5 µM or more.

(6) Template Nucleic Acid Fragment

In the present invention, template nucleic acid (DNA or RNA) may be any of genomic DNA, cDNA, synthetic DNA, mRNA, and total RNA. Nucleic acid that is prepared from a sample that may contain template nucleic acid may also be used. A sample that may contain template nucleic acid may also be directly used intact. Examples of the type of a sample containing template nucleic acid are not particularly limited and include body fluids (e.g., whole blood, serum, urine, cerebrospinal fluid, seminal fluid, and saliva), tissues (e.g., cancer tissue), in vivo derived samples such as cell culture products, nucleic acid-containing samples such as viruses, bacteria, fungi, yeast, plants, and animals, samples that may be contaminated with microorganisms (e.g., foods), or samples in an environment such as soil or waste water. When nucleic acid is prepared from a sample described above, the preparation method therefor is not particularly limited. For example, methods known by persons skilled in the art can be used, including treatment using a surfactant, ultrasonication, purification using glass beads, and the like. Purification of nucleic acid from such a sample can be performed by phenol extraction, chromatography, gel electrophoresis, density gradient centrifugation, or the like.

For amplification of nucleic acid having an RNA-derived sequence, the method of the present invention can be implemented using cDNA as a template that is synthesized by a reverse transcription reaction using the RNA as a template. A primer to be used for a reverse transcription reaction may be a primer having a nucleotide sequence complementary to a specific template RNA, an oligo dT primer, or a primer having a random sequence. The length of a primer for reverse transcription preferably ranges from approximately 6 to 100 nucleotides and flier preferably ranges from 9 to 50 nucleotides. Examples of an enzyme that can be used for a reverse transcription reaction are not particularly limited, as long as such an enzyme has activity of synthesizing cDNA with the use of template RNA and include avian myeloblastosis virus-derived reverse transcriptase (AMV RTase), moloney murine leukemia virus-derived reverse transcriptase (MMLV RTase), and rous associated virus 2 reverse transcriptase (RAV-2 RTase). Furthermore, strand displacement-type DNA polymerase that also has reverse transcription activity can also be used.

In the present invention, double-stranded DNA such as genomic DNA or a nucleic acid amplification fragment and single-stranded DNA such as cDNA that is prepared from RNA via a reverse transcription reaction can be used as template DNAs. The above double-stranded DNA can be used for the method of the present invention after it has been denatured to single-stranded DNAs or can also be used for the method of the present invention without performing such denaturation.

(7) Pretreatment of Template Nucleic Acid

The template nucleic acid in the present invention may be used after being subjected to pretreatment.

The reagent used for the pretreatment may contain, for example, a surfactant, an inhibitor of blood coagulation, a protease, or a lipase. The solution of the reagent may be acidic or alkaline.

The pretreatment may contain a step of heating at a high temperature (for example, 98° C.) or a step of treatment with a denaturing agent. Further, the pretreatment may contain a step of rapidly cooling to 4° C. or less after heating at a high temperature.

(8) Melting Temperature Adjusting Agent

A melting temperature adjusting agent can be added to a reaction solution in the present invention. Specific examples of such a melting temperature adjusting agent include dimethyl sulfoxide (DMSO), betaine, formamide or glycerol, tetraalkyl ammonium salt, and a mixture of two or more types thereof. The dose for melting temperature adjustment is not particularly limited. In the case of DMSO, form amide, or glycerol, a melting temperature adjusting agent can be generally contained accounting for 10% or less of a reaction solution.

Betaine or tetraalkyl ammonium salt can be added at a concentration ranging from approximately 0.2 M to 3.0 M, preferably approximately 0.5 M to 1.5 M, (9) Buffer Component A reaction solution in the present invention can contain a buffer component. Examples of such a buffer component that can be used herein include, but are not particularly limited to, bicin, tricine, hepes, tris, and phosphate (e.g., sodium phosphate and potassium phosphate). The final concentration of such a buffer component ranges from 5 mM to 100 mM and particularly preferably ranges from 10 mM to 50 mM. Regarding pH, such a buffer component having pH generally ranging from 6.0 to 9.0 and particularly preferably ranging from 7.0 to 9.0 can be used, depending on optimum pH for an enzyme to be used for an amplification reaction.

(10) Fluorescent Dye

The reaction solution used in the present invention may contain a fluorescent dye. Examples of a fluorescent dye may include, but are not particularly limited to, SYBR Green I.

(11) Nucleic Acid Amplification Method According to the Present Invention

Next, the nucleic acid amplification method according to the present invention will be described. According to the present invention, a reaction solution containing at least one type of deoxynucleotide triphosphate, at least one type of DNA polymerase, a divalent cation, at least two types of oligonucleotide primer, and a template nucleic acid fragment is incubated. Thus, a polymerase reaction that initiates from the 3' end of the primer is performed, so that the nucleic acid fragment can be amplified. Preferably in the present invention, a step of amplifying the nucleic acid fragment can be carried out substantially isothermally. A temperature for incubation of the reaction solution is preferably a room temperature or higher, more preferably 50° C. or higher and more preferably 55° C. or higher. For example, incubation can be performed at approximately 60° C. Preferably the temperature ranges from approximately 50° C. to approximately 70° C. and further preferably ranges from approximately 55° C. to approximately 65° C., for example. In this case, nonspecific annealing of the primers is suppressed, specificity for DNA amplification is improved, and the secondary structure of template DNA is dissolved. Hence, the elongation activity of DNA polymerase is also improved. The nucleic acid amplification method according to the present invention can be implemented substantially isothermally. "Isothermal or isothermally" in the present invention means that each step is performed at a substantially constant temperature without any significant changes in reaction temperature of each step.

In the present invention, the time required for substantially isothermal incubation of a reaction solution is not particularly limited, as long as a target nucleic acid fragment can be amplified. The time for incubation can be determined to be 5 minutes or more and 12 hours or less, for example. The time for incubation is preferably 5 minutes or more and 2 hours or less, more preferably 5 minutes or more and 60 minutes or less, and further preferably 5 minutes or more and 30 minutes or less. The time for incubation can also be 5 minutes or more and 15 minutes or less.

When a step of amplifying the nucleic acid fragment is carried out substantially isothermally, one of the advantages is that there is no need to raise or lower the temperature. Conventional PCR methods require to raise or lower the temperature. For example, such conventional PCR methods require a reaction apparatus such as a thermal cycler. However, the method of the present invention can be implemented with only an apparatus capable of maintaining a constant temperature.

(12) Application of the Nucleic Acid Amplification Method According to the Present Invention The nucleic acid amplification method according to the present invention can be used for nucleic acid detection, labeling, nucleotide sequence determination, detection of nucleotide mutation (including detection of single nucleotide polymorphism, for example), and the like. The nucleic acid amplification method of the present invention does not require the use of a reaction apparatus capable of performing temperature regulation. Thus, an amplification reaction can be performed according to the method using a large amount of a reaction solution.

Amplified products obtained by the nucleic acid amplification method of the present invention can be detected by methods known by persons skilled in the art. For example, according to gel electrophoresis, gel is stained with ethidium bromide and then reaction products of a specific size can be detected. As detection systems for detection of amplified products, fluorescence polarization, immunoassay, fluorescent energy transfer, enzyme labels (e.g., peroxidase and alkaline phosphatase), fluorescent labels (e.g., fluorescein and rhodamine), chemiluminescence, bioluminescence, or the like can be used. Also, Taqman probes and Molecular Beacon can be used for detection. Amplified products can also be detected using a labeled nucleotide labeled with biotin or the like. In such a case, biotin in an amplified product can be detected using fluorescence labeled avidin, enzyme-labeled avidin, or the like. In addition, amplified products can be detected by an electrode with the use of a redox intercalator known to persons skilled in the art. Alternatively, an SPR may be used to detect amplified products.

Also, nucleic acid amplification can be detected by detecting magnesium pyrophosphate. In such a case, detection can be carried out by a method involving detection based on turbidity or the like, which is known to persons skilled in the art.

The present invention will be specifically described in the following examples. However, the examples are not intended to limit the present invention.

EXAMPLE

Example 1

Nucleic Acid Amplification by Primer having a Tag (Effect of the Position of Tag)

(1) Preparation of Nucleic Acid Sample Solution Containing Target Nucleic Acid Fragment 3.0 ng of Hunan Genomic DNA (produced by Clontech) was heated at 98° C. for 3 minutes to be single-stranded, and a sequence in a β2AR gene was then amplified under the following conditions.

<Primers>

Primers were designed using a β2AR gene as a target. Each primer sequence is as shown below.

```
Primer (1) (Forward 1):
5'-CCACGACGCTTGCTGGCACCCAATA-3'     (SEQ ID NO:1)

Primer (2) (forward 2):
5'-GGCAGGAACTTGCTGGCACCCAATA-3'     (SEQ ID NO:2)

Primer (3) (Forward 3):
5'-TGGGTGGTCTTGCTGGCACCCAATA-3'     (SEQ ID NO:3)

Primer (4) (Reverse)
5'-CCGGCGCATGGCTT-3'                 (SEQ ID NO:4)
```

Details of the positional relationship of the aforementioned primers to the β2AR gene are as shown in FIG. 4.

8 nucleotides (Tag) at 5' end of the primers (1), (2) and (3) are substantially identical with each sequence downstream of the sequence which is substantially identical with the 3' end region of the primer (1), (2) and (3).

(2) Nucleic Acid Amplification Reaction

The amplification reaction was performed at 60° C. for 60 minutes with the composition of a reaction solution shown below. Bst. DNA polymerase (NEB (New England Biolabs)) was used as an enzyme.

| <Composition of reaction solution> | |
|---|---|
| 10 × Bst Buffer (DF) | 1.0 µL |
| 100 mM MgSO4 | 0.6 µL |
| 10% (v/v) Tween 20 | 0.1 µL |
| 100% DMSO | 0.5 µL |
| 25 mM dNTP each | 0.56 µL |
| SYBR Green I (2000 times) | 0.2 µL |
| 50 µM primer (1), (2) or (3) | 0.64 µL |
| 50 µM primer (4) | 0.64 µL |
| Bst. Polymerase | 0.4 µL |
| Nucleic acid fragment sample solution obtained in (1) | 0.4 µL |
|  | 3.0 ng |
| Purified water | 4.96 µL |
|  | 10.0 µL |

(3) Detection of Amplified Product

Figure 5:
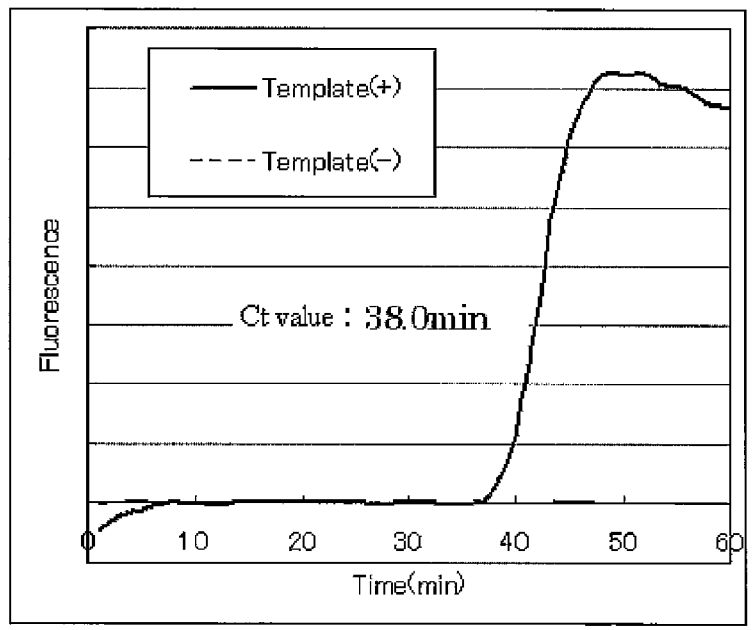
FIG. 5 shows results of fluorescence detection of an amplified product obtained as a result of the amplification reaction of the present invention.
Figure 6:
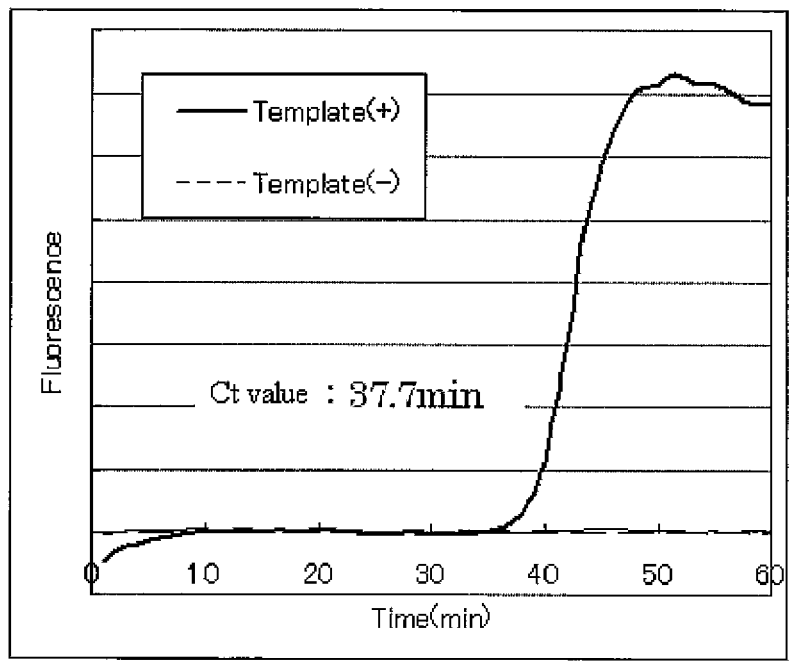
FIG. 6 shows results of fluorescence detection of an amplified product obtained as a result of the amplification reaction of the present invention.
Figure 7:
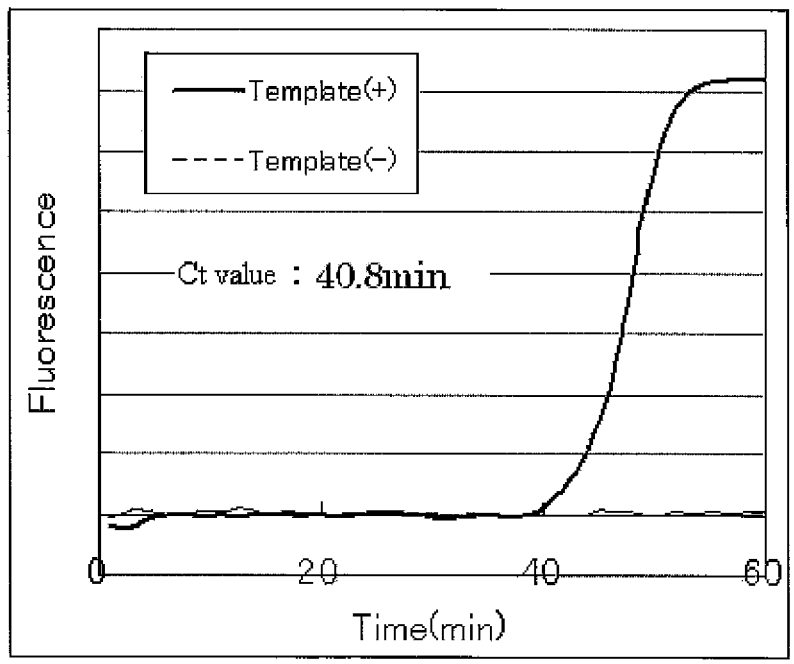
FIG. 7 shows results of fluorescence detection of an amplified product obtained as a result of the amplification reaction of the present invention.

The amplification reaction in (2) above was carried out using a real-time fluorescence detection apparatus (Mx3000p, manufactured by Stratagene), and the fluorescence was detected. The results are shown in FIGS. 5 to 7.

It is shown that a nucleic acid amplification reaction from a sample derived nucleic acid specimen can be detected in real time. The time (Ct value) when an amount of fluorescence had reached 250 in the above graph was calculated using Mx3000p analysis software. The results are shown in Table 1.

TABLE 1

| Forard Primer | Reverse Primer | Ct Value [minute] |
|---|---|---|
| Primer (1) | Primer (4) | 38.0 |
| Primer (2) | Primer (4) | 37.7 |
| Primer (3) | Primer (4) | 40.8 |

(4) Electrophoresis of Amplified Products

Figure 8:
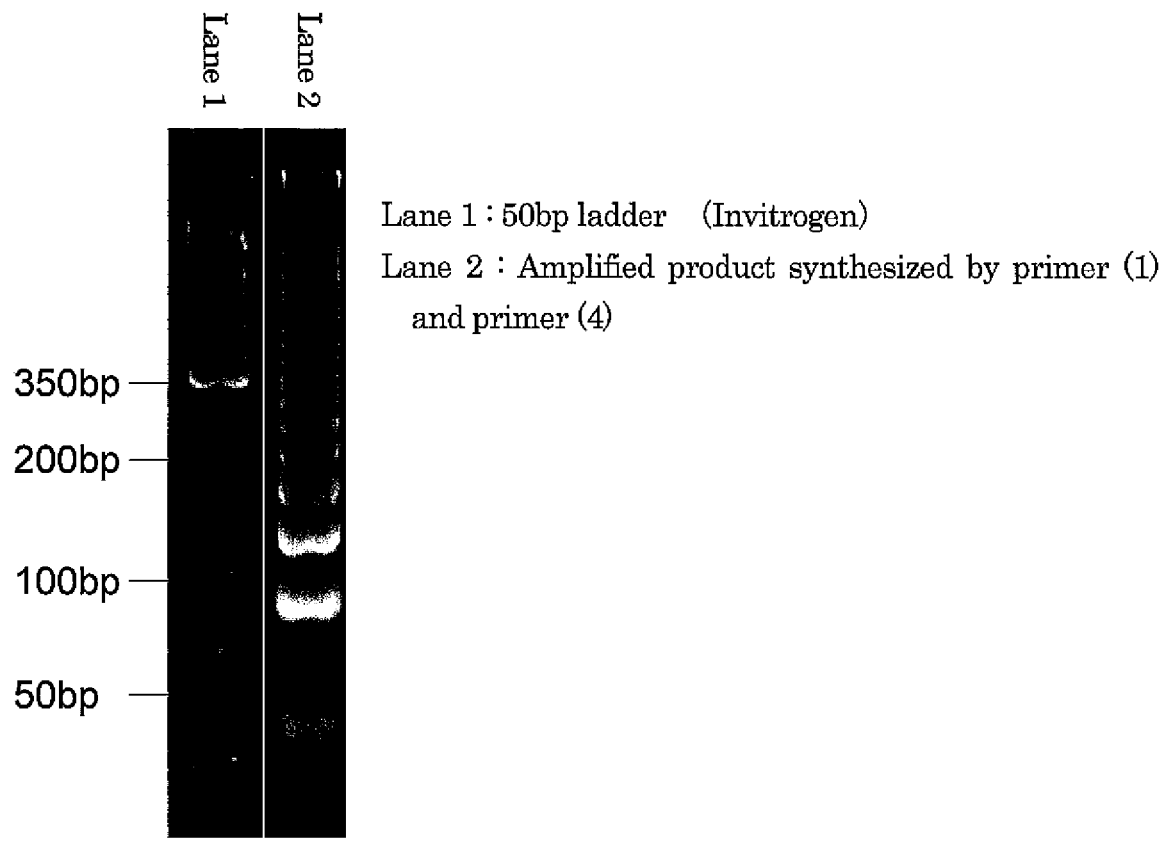
FIG. 8 shows the results of electrophoresis of an amplified product obtained as a result of the amplification reaction of the present invention.
Figure 9:
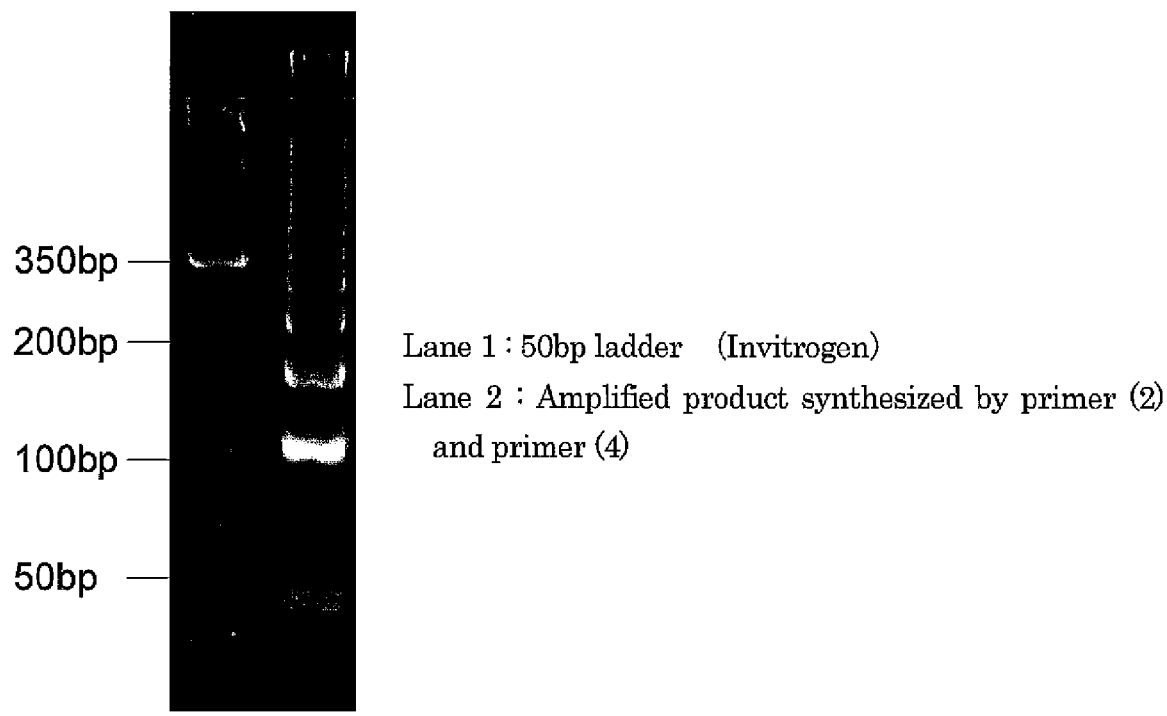
FIG. 9 shows the results of electrophoresis of an amplified product obtained as a result of the amplification reaction of the present invention.
Figure 10:
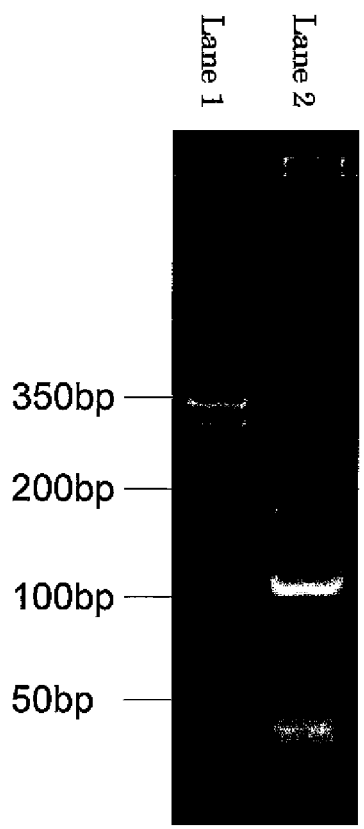
FIG. 10 shows the results of electrophoresis of an amplified product obtained as a result of the amplification reaction of the present invention.

Electrophoresis was performed at 100 V for 60 minutes using 3 wt % agarose gel and 0.5×TBE buffer (50 mM Tris, 45 mM Boric acid, and 0.5 mM EDTA, pH 8.4). The results are shown in FIGS. 8 to 10.

Ladder-like regular electrophoresis patterns were obtained in any combination of the primers. These results show that regular amplified products are obtained. Namely, it is shown that an amplification reaction can be controlled.

(5) Sequence Analysis of Amplified Product

The amplified product was purified by NucleoSpin® Extract II (manufactured by MACHEREY-NAGEL), and was incorporated into a vector using TOPO TA Cloning Kit (manufactured by Invitrogen). *Escherichia coli* was then transformed with the vector. The transformed *Escherichia coli* was cultured in an LB medium containing ampicillin.

Thereafter, plasmid DNA was recovered from the cultured *Escherichia coli*, using QIAprep Miniprep (manufactured by Qiagen).

The recovered plasmid DNA was sequenced to determine the nucleotide sequence thereof. The sequencing was carried out by using ABI PRISM 310 Genetic Analyzer (manufactured by ABI). An M13 Reverse Primer was used as a primer.

```
M13 Reverse Primer
5'-CAGGAAACAGCTATGAC-3'           (SEQ ID NO:5)
```

As a result of the sequencing, it was found that the nucleic acids having the following sequences were present in the amplified product obtained by a combination of Primer (1) and Primer (4),

```
                                    (SEQ ID NO: 21)
(1)
                                    (SEQ ID NO:6)
5'-CCACGACGTT CTTGCTGGCA CCCAATAGAA GCCATGCGCC

GG-3'

3'-GGTGCTGCAA GAACGACCGT GGGTTATCTT CGGTACGCGG

CC-5'

(42 base pairs)

(SEQ ID NO: 22)
(2)
                                    (SEQ ID NO:7)
5'-CCACGACGTT CTTGCTGGCA CCCAATAGAA GCCATGCGCC

GGACCACGAC-3'

3'-GGTGCTGCAA GAACGACCGT GGGTTATCTT CGGTACGCGG

CCTGGTGCTG-5'

5'-GTTCTTGCTG GCACCCAATA GAAGCCATGC GCCGG-3'

3'-CAAGAACGAC CGTGGGTTAT CTTCGGTACG CGGCC-5'

(85 base pairs)

(SEQ ID NO: 23)
(3)
                                    (SEQ ID NO:8)
5'-CCACGACGTT CTTGCTGGCA CCCAATAGAA GCCATGCGCC

GGACCACGAC-3'

3'-GGTGCTGCAA GAACGACCGT GGGTTATCTT CGGTACGCGG

CCTGGTGCTG-5'

5'-GTTCTTGCTG GCACCCAATA GAAGCCATGC GCCGGACCAC

GACGTTCTTG-3'

3'-CAAGAACGAC CGTGGGTTAT CTTCGGTACG CGGCCTGGTG

CTGCAAGAAC-5'

5'-CTGGCACCCA ATAGAAGCCA TGCGCCGG-3'

3'-GACCGTGGGT TATCTTCGGT ACGCGGCC-5'

(128 base pairs)
```

The chain lengths of the amplified products obtained by sequencing corresponded to the electrophoretic results as shown in FIG. 8.

The amplified product (1) was a region sandwiched between two primers.

The amplified product (2) was obtained as a result that amplified products were bound to one another via hybridization between the 5' end sequence (Tag) of Forward primer and the upstream sequence of Reverse primer The amplified product (2) had a structure of "a region sandwiched between two primers"+"a sequence between Reverse Primer and Tag sequence"+"a region sandwiched between two primers". (this is hereinafter referred to as dimer)

The amplified product (3) was obtained as a result that amplified products were bound to one another via hybridization between the 5' end sequence (Tag) of Forward primer and the upstream sequence of Reverse primer, as in the amplified product (2). The amplified product (3) had a structure of "a region sandwiched between two primers"+"a sequence between Reverse Primer and Tag sequence"+"a region sandwiched between two primers"+"a sequence between Reverse Primer and Tag sequence"+"a region sandwiched between two primers". (this is hereinafter referred to as trimer)

As a result of the sequencing, it was found that the nucleic acids having the following sequences were present in the amplified product obtained by a combination of Primer (2) and Primer (4),

```
                                    (SEQ ID NO: 24)
(1)
                                    (SEQ ID NO:9)
5'-GGCACGAGTT CTTGCTGGCA CCCAATAGAA GCGATGCGGC

GG-3'

3'-GCGACGAGAA GAACGACCGT GGGTTATCTT CGGTACGCGG

CC-5'

(42 base pairs)
```

(SEQ ID NO: 25)

(2)

(SEQ ID NO:10)
5'-GGGACGAGTT CTTGCTGGCA CCCAATAGAA GCCATGCGCC

GGACCACGAC-3'

3'-CCCTGCTCAA GAACGACCGT GGGTTATCTT CGGTACGCCG

CCTGGTGCTG-5'

5'-GTCACGCAGG AAAGGGACGA GTTCTTGCTG GCACCCAATA

GAAGCCATGC-3'

3'-CAGTGCGTCC TTTCCCTGCT CAAGAACGAC CGTGGGTTAT

CTTCGGTACG-5'

5'-GCCGG-3'

3'-CGGCC-5'

(105 base pairs)

(SEQ ID NO: 26)

(3)

(SEQ ID NO:11)
5'-GGGACGAGTT CTTGCTGGCA CCCAATAGAA GCCATGCGCC

GGACCACGAC-3'

3'-CCCTGCTCAA GAACGACCGT GGGTTATCTT CGGTACGCGG

CCTGGTGCTG-5'

5'-GTCACGCAGG AAAGGGACGA GTTCTTGCTG GCACCCAATA

GAAGCCATGC-3'

3'-CAGTGCGTCC TTTCCCTGCT CAAGAACGAC CGTGGCTTAT

CTTCGGTACG-5'

5'-GCCGGACCAC GACGTCACGC AGGAAAGGGA CGAGTTCTTG

CTGGCAGCCA-3'

3'-CGGCCTGGTG CTGCAGTGCG TCCTTTCCCT GCTCAAGAAC

GACCGTGGGT-5'

5'-ATAGAAGCCA TGCGCCGG-3'

3'-TATCTTCGGT ACGCGGCC-5'

(168 base pairs)

The chain lengths of the amplified products obtained by sequencing corresponded to the electrophoretic results as shown in FIG. 9.

The amplified product (1) was a region sandwiched between two primers.

The amplified product (2) was obtained as a result that amplified products were bound to one another via hybridization between the 5' end sequence (Tag) of Forward primer and the upstream sequence of Reverse primer. The amplified product (2) is a dimmer.

The amplified product (3) was obtained as a result that amplified products were bound to one another via hybridization between the 5' end sequence (Tag) of Forward primer and the 5' upstream sequence of Reverse primer, as in the amplified product (2). The amplified product (3) is a trimer.

As a result of the sequencing, it was found that the nucleic acids having the following sequences were present in the amplified product obtained by a combination of Primer (3) and Primer (4), (SEQ ID NO: 27)

(1)

(SEQ ID NO:12)
5'-TGGGTGGTTT CTTGCTGGCA CCCAATAGAA GCCATGCGCC

GG-3'

3'-ACCCACCAAA GAACGACCGT GGGTTATCTT CGGTACGGGG

CC-5'

(42 base pairs)

(SEQ ID NO: 28)

(2)

(SEQ ID NO:13)
5'-TGGGTGGTTT CTTGCTGGCA CCCAATAGAA GCCATGCGCC

GGACCACGAC-3'

3'-ACCCACCAAA GAACGACCGT GGGTTATCTT CGGTACGCGG

CCTGGTGCTG-5'

5'-GTCACGCAGG AAAGGGACGA GGTGTGGGTG GTTTCTTGCT

GGCACCCAAT

3'-CAGTGCGTCC TTTCCCTGCT CCACACCCACCAAAGAACGAC

CGTGGGTTA

5'-AGAAGCCATG CGCCGG-3'

3'-TCTTCGGTAC GCGGCC-5'

(116 base pairs)

(SEQ ID NO: 29)

(3)

(SEQ ID NO:14)
5'-TGGGTGGTTT CTTGCTGGCA CCCAATAGAA GCCATGCGCC

GGACCACGAC-3'

3'-ACCCACCAAA GAACGACCGT GGGTTATCTT CGGTACGCGG

CCTGGTGCTG-5'

5'-GTCACGCAGG AAAGGGACGA GGTGTGGGTG GTTTCTTGCT

GGCACCCAAT-3'

3'-CAGTGCGTCC TTTCCCTGCT CCACACCCAC CAAAGAACGA

CCGTGGGTTA-5'

5'-AGAAGCCATG CGCCGGACCA CGACGTCACG CAGGAAAGGG

ACGAGGTGTG-3'

3'-TCTTCGGTAC GCGGCCTGGT GCTGCAGTGC GTCCTTTCCC

TGCTCCACAC-5'

5'-GGTGGTTTCT TGCTGGCACC CAATAGAAGC CATGCGCCGG--3'

3'-CCACCAAAGA ACGACCGTGG GTTATCTTCG GTACGCGGCC-5'

(190 base pairs)

The chain lengths of the amplified products obtained by sequencing corresponded to the electrophoretic results as shown in FIG. 10.

The amplified product (1) was a region sandwiched between two primers.

The amplified product (2) was obtained as a result that amplified products were bound to one another via hybridization between the 5' end (Tag) of Forward primer and the upstream sequence of Reverse primer. The amplified product (2) is a dimmer.

The amplified product (3) was obtained as a result that amplified products were bound to one another via hybridization between the 5' end sequence (Tag) of Forward primer and the upstream sequence of Reverse primer, as in the amplified product (2). The amplified product (3) is a trimer.

It was found that polymer products were formed via Tag in any amplified products. Namely, it was possible to form polymer products positively and control the amplification reaction by adding, at the 5' end of the first oligonucleotide primer, a nucleotide sequence on the template nucleic acid fragment which is present downstream of the sequence which is substantially identical with the 3' end region of the first oligonucleotide primer (the region of the first oligonucleotide primer where it is annealed to the template nucleic acid).

Example 2

Nucleic Acid Amplification by Primer having a Tag (Effect of the Length of Tag)

(1) Preparation of Nucleic Acid Sample Solution Containing Target Nucleic Acid Fragment 3.0 ng of Human Genomic DNA (produced by Clontech) was heated at 98° C. for 3 minutes to be single-stranded, and a sequence in a β2AR gene was then amplified under the following conditions.

<Primers>

Primers were designed using a β2AR gene as a target. Each primer sequence is as shown below.

```
Primer (5) (Forward5):
                                         (SEQ ID NO:15)
5'-TGGTCTTGCTGGCACCCAATA-3'

Primer (6) (Forward6):
                                         (SEQ ID NO:16)
5'-TGGGTGGTCTTGCTGGCACCCAATA-3'

Primer (7) (Forward7):
                                         (SEQ ID NO:17)
5'-TGGGTGGTGGGCCTTGCTGGCACCCAATA-3'

Primer (8) (Forward8):
                                         (SEQ ID NO:18)
5'-TGGGTGGTGGGCATCTTGCTGGCACCCAATA-3'

Primer (9) (Revesre2):
                                         (SEQ ID NO:19)
5'-TCCCTTTCCTGCGTGAC-3'
```

Figure 11:
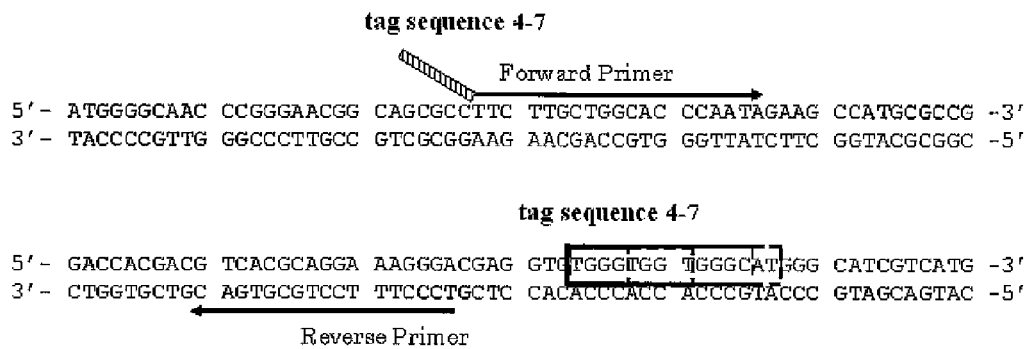
FIG. 11 shows in detail the positional relationship of the primers used in the Examples and β2AR gene (SEQ ID NOS: 30 and 31).

Details of the positional relationship of the aforementioned primers to the P2AR gene are as shown in FIG. 11.

A nucleotide sequence (Tag) which is substantially complementary with 4 nucleotides, 8 nucleotides, 12 nucleotides or 14 nucleotides which are respectively present upstream of the sequence which is substantially identical with Primer (9), is added at the 5' terminal of Primer (5), Primer (6), Primer (7) or Primer (8).

(2) Nucleic Acid Amplification Reaction

The amplification reaction was performed at 60° C. for 60 minutes with the composition of a reaction solution shown below. Bst. DNA polymerase (NEB (New England Biolabs)) was used as an enzyme.

| <Composition of reaction solution> | |
|---|---|
| 10 × Bst Buffer (DF) | 1.0 μL |
| 100 mM MgSO4 | 0.6 μL |
| 10% (v/v) Tween 20 | 0.1 μL |
| 100% DMSO | 0.5 μL |
| 25 mM dNTP each | 0.56 μL |
| SYBR Green I (2000 times) | 0.2 μL |
| 50 μM primer (5), (6), (7) or (8) | 0.64 μL |
| 50 μM primer (9) | 0.64 μL |
| Bst. Polymerase | 0.4 μL |
| Nucleic acid fragment sample solution obtained in (1) | 0.4 μL  3.0 ng |
| Purified water | 4.96 μL |
| | 10.0 μL |

(3) Electrophoresis of Amplified Products

Figure 12:
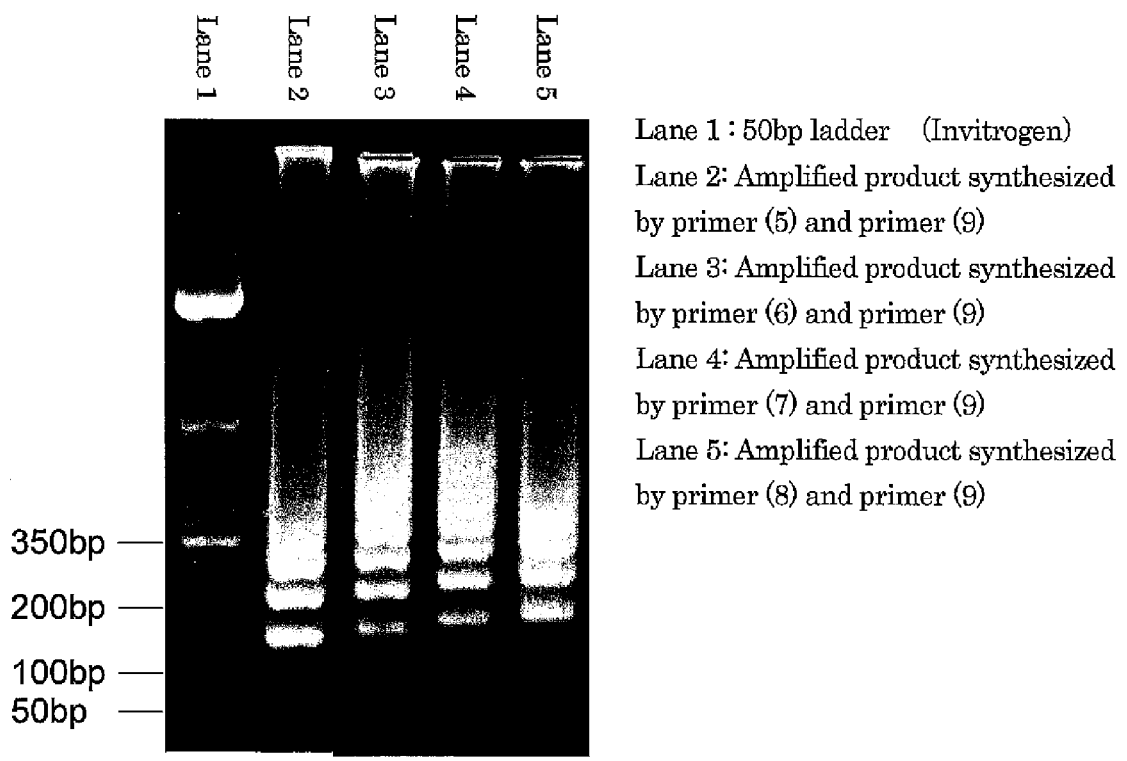
FIG. 12 shows the results of electrophoresis of an amplified product obtained as a result of the amplification reaction of the present invention.

Using the aforementioned amplified product, electrophoresis was performed at 100 V for 60 minutes using 3 wt % agarose gel and 0.5×TBE buffer (50 mM Tris, 45 mM Boric acid, and 0.5 mM EDTA, pH 8.4). The results are shown in FIG. 12.

Ladder-like regular electrophoresis patterns were obtained in any combination of the primers. These results show that regular amplified products are obtained. It is considered that polymer products via Tag are formed in the same way as in Example 1. Namely, it is shown that an amplification reaction can be controlled.

Comparative Example 1

As a comparative example, a nucleic amplification reaction is described in a system where a nucleotide sequence on the template nucleic acid fragment which is present downstream of the sequence which is substantially identical with the 3' end region of the first oligonucleotide primer (the region of the first oligonucleotide primer where it is annealed to the template nucleic acid), is not added at the 5' terminal side of the first oligonucleotide primer (1) Preparation of Nucleic Acid Sample Solution Containing Target Nucleic Acid Fragment 3.0 ng of Human Genomic DNA produced by Clontech) was heated with a pretreatment solution (30 mM NaOH, 0.05% Tween 20) at 98° C. for 3 minutes to be single-stranded, and a sequence in a β2AR gene was then amplified under the following conditions.

<Primers>

Primers were designed using a β2AR gene as a target. Each primer sequence is as shown below.

```
Primer (1) (Forward):
5'-CTTGCTGGCACCCAATA-3'      (SEQ ID NO:20)

Primer (2) (Reverse):
5'-CCGGCGCATGGCTT-3'         (SEQ ID NO:4)
```

Details of the positional relationship of the aforementioned primers to the β2AR gene are as shown in FIG. 13.

(2) Nucleic Acid Amplification Reaction

The amplification reaction was performed at 60° C. for 60 minutes with the composition of a reaction solution shown below. Bst, DNA polymerase (NEB (New England Biolabs)) was used as an enzyme.

<Composition of reaction solution>

| | |
|---|---|
| 10 × Bst Buffer(DF) | 1.0 µL |
| 100 mM MgSO4 | 0.6 µL |
| 10%(v/v) Tween20 | 0.1 µL |
| 100% DMSO | 0.5 µL |
| 25 mM dNTP each | 0.56 µL |
| SYBR Green I (2000 times) | 0.2 µL |
| 50 µM primer(1) | 0.64 µL |
| 50 µM primer(2) | 0.64 µL |
| Bst. Polymerase | 0.4 µL |

-continued

<Composition of reaction solution>

| | |
|---|---|
| Nucleic acid fragment sample solution obtained in (1) (3.0 ng) | 0.4 µL |
| Purified water | 4.96 µL |
| | 10.0 µL |

(3) Electrophoresis of Amplified Products

Using the aforementioned amplified product, electrophoresis was performed at 100 V for 60 minutes using 3 wt % agarose gel and 0.5×TBE buffer (50 mM Tris, 45 mM Boric acid, and 0.5 mM EDTA, pH 8.4). The results are shown in FIG. 14.

Generally, smear-like electrophoresis patterns were obtained, although slight regularity is observed. Namely, it was found that the regularity of polymer formation reaction was low.

The invention claimed is:

1. A nucleic acid amplification method, comprising:
   (a) providing a reaction solution containing
       (i) at least one type of deoxynucleotide triphosphate,
       (ii) a DNA polymerase having a strand displacement activity,
       (iii) a single-strand template DNA, or a double-strand template DNA including said single-strand template DNA as one strand,
       (iv) a forward primer that anneals to the single-strand template DNA, and
       (v) a reverse primer that anneals to a forward primer extension product; and
   (b) incubating the reaction solution to amplify the single-strand template DNA or the double-strand template DNA, wherein
   the forward primer includes a tag sequence at a 5' end region, and
   the tag sequence is complementary to a portion of the single-stranded template DNA, said portion being present 5' upstream of a portion of the single-stranded template DNA where a 3' end region of the forward primer anneals.

2. The nucleic acid amplification method of claim 1, wherein the tag sequence is a nucleotide sequence present 3' downstream of a portion of the forward primer extension product where the reverse primer anneals.

3. The nucleic acid amplification method of claim 1, wherein the tag sequence consists of 2 to 20 nucleotides.

4. The nucleic acid amplification method of claim 1, wherein the tag sequence is a nucleotide sequence which is present within a region of the forward primer extension product, said region consisting of 200 nucleotides or less present 3' downstream of a portion of the forward primer extension product where said portion is complementary to the portion of the single-stranded template DNA where a 3' end region of the forward primer anneals.

5. The nucleic acid amplification method of claim 1, wherein the reaction solution further contains at least 0.01% or more surfactant.

6. The nucleic acid amplification method of claim 5, wherein the surfactant is a nonionic surfactant.

7. The nucleic acid amplification method of claim 6, wherein the nonionic surfactant is at least one selected from the group consisting of a polyoxyethylene sorbitan fatty acid ester-based surfactant, and a polyoxyethylene alkyl ether-based surfactant.

8. The nucleic acid amplification method of claim 1, wherein the reaction solution further contains a divalent cation.

9. The nucleic acid amplification method of claim 1, wherein the reaction solution further contains a melting temperature adjusting agent.

10. The nucleic acid amplification method of claim 9, wherein the melting temperature adjusting agent is dimethyl sulfoxide, betaine, formamide, or glycerol, or a mixture of two or more types thereof.

11. The nucleic acid amplification method of claim 1, wherein the DNA polymerase is at least one selected from the group consisting of a *Bacillus stearothermophilus*-derived 5'→3' exonuclease-deficient DNA polymerase, a *Bacillus caldotenax*-derived 5'→3' exonuclease-deficient DNA polymerase, a *Thermococcus litoralis*-derived 5'→3' exonuclease-deficient DNA polymerase, and an *Alicyclobacillus acidocaldarius*-derived DNA polymerase.

12. The nucleic acid amplification method of claim 1, wherein the reaction solution is incubated at a substantially isothermal temperature in Step (b).

13. The nucleic acid amplification method of claim 1, wherein the reaction solution is incubated at a substantially isothermal temperature of 50° C. to 100° C.

14. The nucleic acid amplification method of claim 1, wherein the reaction solution is incubated within 60 minutes in Step (b).

* * * * *